United States Patent
Receveur et al.

(10) Patent No.: US 8,340,769 B2
(45) Date of Patent: Dec. 25, 2012

(54) IMPLANTABLE TEMPERATURE SENSOR

(75) Inventors: Rogier Receveur, Maastricht (NL); Vincent Larik, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 254 days.

(21) Appl. No.: 12/795,895

(22) Filed: Jun. 8, 2010

(65) Prior Publication Data

US 2010/0249872 A1 Sep. 30, 2010

Related U.S. Application Data

(63) Continuation of application No. 10/781,245, filed on Feb. 18, 2004, now Pat. No. 7,756,581.

(51) Int. Cl.
*A61N 1/00* (2006.01)
(52) U.S. Cl. ......................................................... 607/37
(58) Field of Classification Search ................. 607/37
See application file for complete search history.

(56) References Cited

U.S. PATENT DOCUMENTS

| | | | |
|---|---|---|---|
| 3,589,360 | A | 6/1971 | Sinclair |
| 4,419,999 | A | 12/1983 | May, Jr. et al. |
| 4,543,954 | A | 10/1985 | Cook et al. |
| 5,022,766 | A | 6/1991 | Phipps |
| 5,081,988 | A | 1/1992 | Cook et al. |
| 5,174,299 | A | 12/1992 | Nelson |
| 5,336,244 | A | 8/1994 | Weijand |
| 5,493,100 | A | 2/1996 | Renger |
| 5,556,421 | A | 9/1996 | Prutchi et al. |
| 5,989,192 | A | 11/1999 | Weijand et al. |
| 6,024,704 | A | 2/2000 | Meador et al. |
| 6,144,866 | A | 11/2000 | Miesel et al. |
| 6,223,081 | B1 | 4/2001 | Kerver |
| 7,263,401 | B2 * | 8/2007 | Scott et al. ............... 607/36 |
| 7,347,826 | B1 | 3/2008 | Karicherla et al. |
| 2002/0165588 | A1 | 11/2002 | Fraley et al. |

\* cited by examiner

*Primary Examiner* — George Manuel
(74) *Attorney, Agent, or Firm* — Evans M. Mburu

(57) ABSTRACT

A sensor is disposed within a pin portion of a feedthrough assembly. The feedthrough assembly provides a hermetically sealed enclosure that protects the sensor. In one embodiment, the sensor is a temperature sensor and the feedthrough assembly thermally isolates the sensor from the surrounding housing or enclosure.

21 Claims, 14 Drawing Sheets

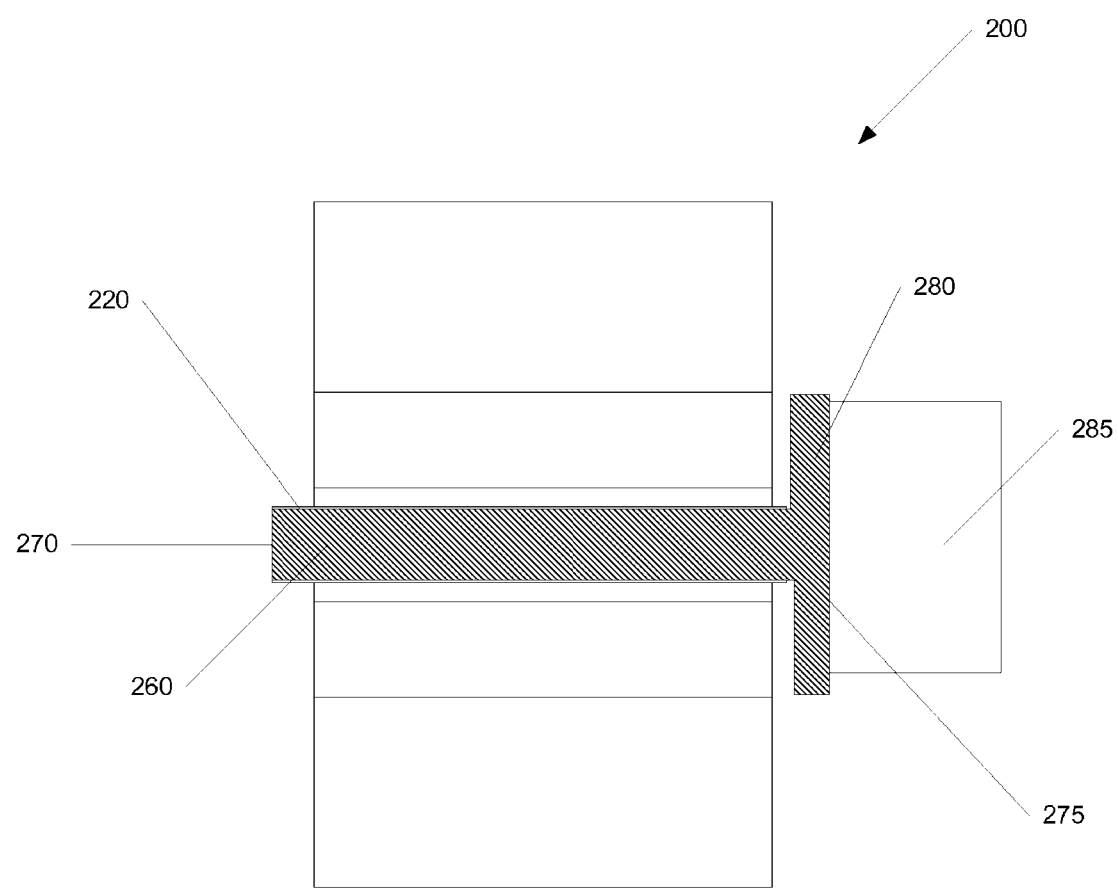

IMPLANTABLE TEMPERATURE SENSOR

This application is a continuation of U.S. application Ser. No. 10/781,245, filed Feb. 18, 2004 now U.S. Pat. No. 7,756,581, the entire content of which is incorporated herein by reference in its entirety.

BACKGROUND OF THE INVENTION

The present invention relates to implantable medical devices. More specifically, the present invention relates to implantable medical devices including sensors.

DESCRIPTION OF THE RELATED ART

Various medical devices exist that utilize a lead to sense signals from or deliver electrical stimulation to cardiac tissue. For example, cardiac pacemakers often utilize a single lead having a distal tip disposed within the right atrium or right ventricle of the heart to sense and pace. Dual chamber devices have a lead in both the ventricle and the atrium and are quite commonly used. Implanting a lead within either right-sided chamber is relatively straightforward and typically presents little complication for a skilled practitioner.

More recently, a benefit has been recognized in pacing, sensing, stimulating or otherwise having communication with the left side of the heart. In general, leads are typically not implanted within the left atrium or left ventricle as oxygenated blood flows from the left side to the remainder of the body. As such, left sided lead placement has undertaken several alternative approaches.

An epicardial lead may be affixed to an external portion of the heart, i.e., the pericardium, at an appropriate location on the left side of the heart. While current techniques are being improved, the difficulty with the use of such epicardial leads is their guidance and manipulation from the implant site, through the chest cavity to the heart, and their affixation. The procedure is at least different, if not more complicated, than standard venous implantation for, e.g., right sided leads.

As such, a venous implantation technique is available and is presently the most commonly used technique for left-sided lead implantations. In summary, a lead is advanced into the right atrium and caused to enter the coronary sinus. The lead is then manipulated through the cardiac vein until it is properly situated against the exterior wall of the left ventricle or left atrium. Because of this disposition within a relatively narrow vein, the lead is often affixed by relying on a wedging action of a biased portion of the lead, though other affixation techniques may be utilized.

One of the more challenging aspects of such an implantation is initially inserting the lead or the guiding mechanism (e.g., catheter, stylet, guidewire) into the ostium of the coronary sinus. In fact, this step often accounts for a great deal of the total implantation time. In addition, the variability in this difficult step between patients leads to great variability in total implant time across patients. In some difficult cases, the coronary sinus cannot be located and the procedure is abandoned in lieu of an epicardial lead placement.

The difficulty in inserting the lead or guiding mechanism into the coronary sinus arises from several different factors. Entry into the right atrium is, as mentioned relatively straight forward. For example, following the superior vena cava will lead directly into the right atrium. However, the right atrium is a relatively large (with respect to the coronary sinus), chamber that is in rhythmic motion. For this reason alone, navigation, especially via remote manipulation, is difficult. In addition, more significant anatomical structures, such as the tricuspid valve or the inferior vena cava are more easily detected and in that sense, provide obstacles to manipulating the device to find the coronary sinus. The position, configuration, and orientation of the coronary sinus often make it somewhat occluded and thus, more difficult to find. Finally, the angle of entry is often not conducive to easy remote manipulation. Wide variation in patient anatomy may greatly affect the scope of any or all of these issues.

The implantation procedure often relies on a fluoroscope to permit the practitioner to view certain anatomical features and the leads current position with respect to those features. Fluoroscopy does not illustrate soft tissue very well and provides virtually no guidance with respect to locating the coronary sinus. Thus, the practitioner is working almost entirely be feel.

Thus, one of the major obstacles in left sided lead implantations, or other left sided procedures, is the initial location of the coronary sinus and the insertion of the lead, guiding mechanism, or other tool therethrough.

BRIEF DESCRIPTION OF THE DRAWINGS

FIG. 15 is a schematic illustration of a pressure sensor housed within a feedthrough assembly.

DETAILED DESCRIPTION

The present invention, in one embodiment is a system and method that provides for the guidance of a device to the ostium of the coronary sinus and/or provides confirmation that the device is located within the coronary sinus. The device is a lead that is being implanted or is a guidance device, such as a catheter, stylet, guidewire or the like that will facilitate the implantation of a lead. The device could also be various other tools such as an ablation electrode or various sensors that are used on a temporary or permanent basis.

The coronary sinus provides an entryway for return blood flow into the right atrium and, as previously indicated, is relatively small with respect to the right atrium. As such, the return blood flow generates a number of physical characteristics. For example, there is a temperature variance between the blood within the coronary sinus and that within the right atrium on the order of about 1° C. More precisely, the temperature differential is usually on the order of about 0.2° C. As such, there is a temperature gradient about the ostium of the coronary sinus. In addition, the pulsitile blood flow generates certain pressure characteristics as well as turbulent flow. The oxygen and/or carbon dioxide levels of the return blood from the coronary sinus are distinguishable from that present in the right atrium. In summary, the nature of the return blood flow from the coronary sinus presents certain detectable physical indicia.

Figure 1:
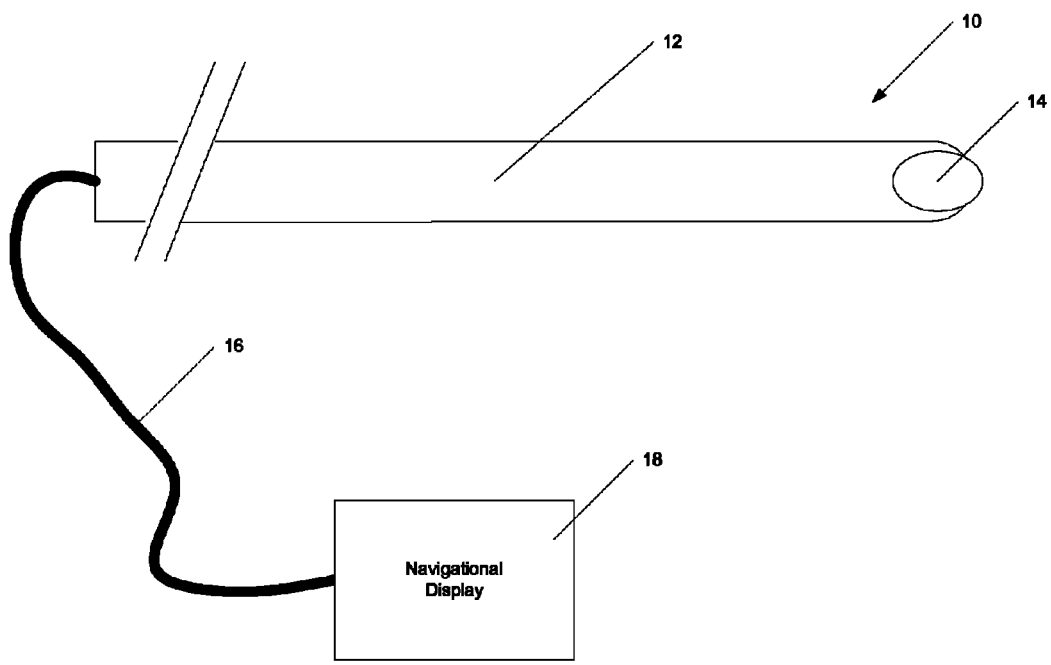
FIG. 1 is a schematic illustration of a lead with a sensor coupled to a navigational display.

FIG. 1 illustrates a lead 10 having a sensor 14 disposed at or near a distal end of the lead 10. The lead 10 has a lead body 12 that carries the sensor 14 and can be manipulated for movement and steerability within the cardiac anatomy. The lead 10 may include various pull wires, a stylet may disposed within the lead 10, the lead 10 may pass over a guidewire, or the lead may be disposed within a catheter or incorporate various other known manipulation devices. In its most basic sense and as used herein, lead 10 is illustrative of any device that can be passed into and guided within the right atrium and then detect and/or enter the coronary sinus, such as, for example, a sensing/pacing/defibrillation lead, a catheter, a stylet, a guidewire, or various other medical delivery or surgical instruments. Depending upon the particular device employed, other elements will be present (e.g., sense/pace electrodes) that are omitted here for clarity.

Lead 10 is communicatively coupled with a navigation control display 18 via electrical connections 16. Navigation control display 18 takes data acquired from the sensor 14 and displays or otherwise presents the data (e.g., audible representations). Alternatively, or in addition thereto, navigation control display 18 processes the data and then displays or presents guidance information.

The sensor 14 may sense any criteria useful for locating the coronary sinus and/or confirming that the sensor 14 is disposed within the coronary sinus. In one embodiment, the sensor 14 is a temperature sensor. In another embodiment, the sensor 14 is for example, a pressures sensor, an oxygen sensor, a chemical sensor (e.g., lactate), senses pH balance, is a velocity sensor that senses flow, is an ultrasound sensor (with or without Doppler capability), or is an optical sensor. For any given parameter, multiple sensor options exist. Pressure, for example, may be sensed via compression of a calibrated element, a piezo-electric sensor, or an optical sensor. Likewise, blood oxygen may be sensed via an optical sensor or a chemical sensor that measures direct levels or derivatives.

As illustrated in FIGS. 2A-2B, the lead 10 may include a plurality of sensors 14A-14E, that can be arranged in any desired configuration. Such a combination of sensors provide an array that facilitate the sensing of, for example, a temperature gradient. Alternatively, different types of sensors may be employed in concert to detect any number and type of indicia. For example, both pressure and temperature may be sensed simultaneously.

Figure 3:
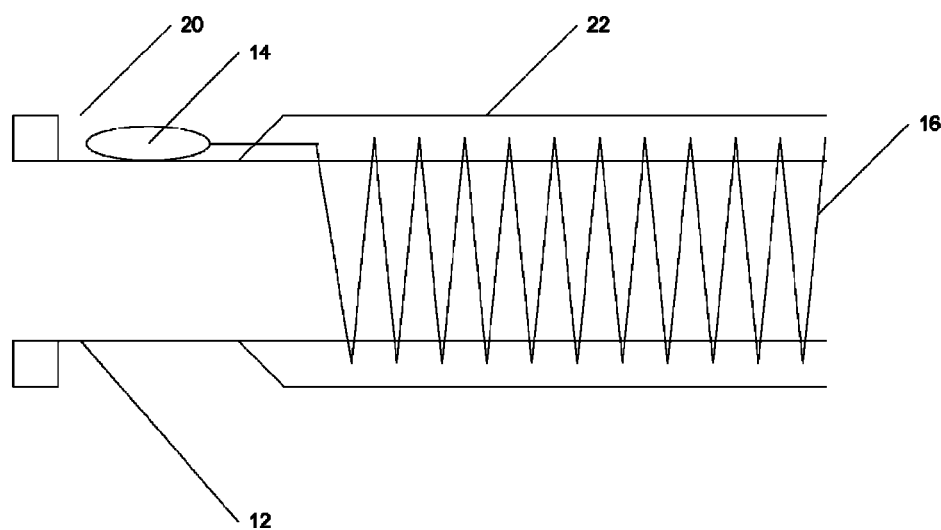
FIG. 3 is a schematic illustration of a sensor coupled with a lead.
Figure 4:
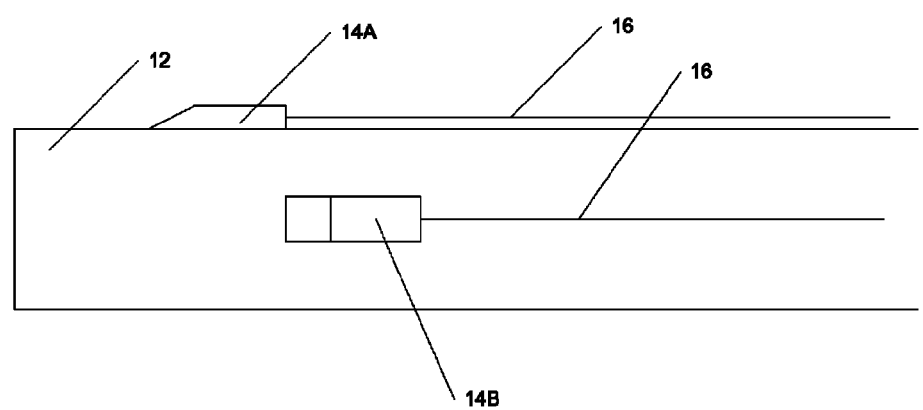
FIG. 4 is a schematic illustration of a plurality of sensors coupled with a lead.

FIGS. 3 and 4 illustrate various ways of coupling the sensor 14 to the lead body 12. For example, external shielding 22 is disposed about the lead body 12 that encases the electrical communication means 16. The electrical communication means 16 includes wires, cables, fiber optics, or any suitable medium for transmitting data obtained from the sensor 14. The sensor 14 is exposed through an opening 20 within the external shielding 22. The external shielding is disposed circumferentially about the lead body 12 in a coaxial arrangement or may form a smaller, linear tubular arrangement disposed on an outer surface of the lead body 12.

Figure 6:
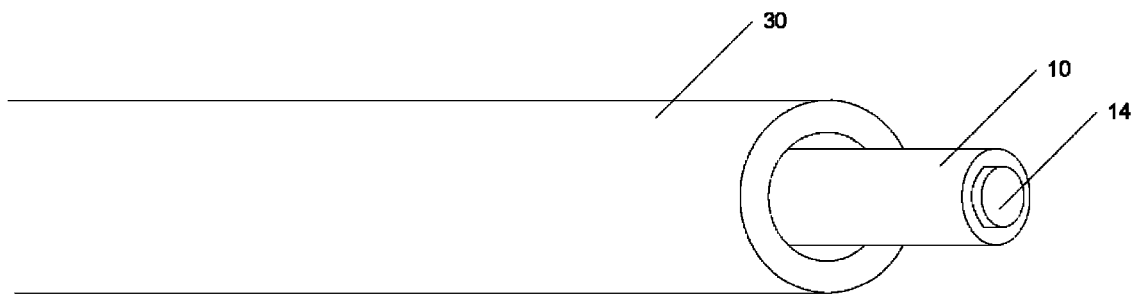
FIG. 6 is a schematic illustration of a lead having a sensor, disposed within a catheter.

FIG. 4 illustrates an embodiment wherein the sensor 14 is affixed to an external portion of the lead body 12 and the electrical communication means 16 includes one or more wires that are axially aligned with the lead body 12. Depending upon the device employed, the sensor 14 may depend externally from or reside within the distal end of the lead 10, reside within an interior portion of the lead 10, depend from any exterior portion of the lead, or be partially exposed through some portion of the lead 10. In addition, the sensor 14 may be selectively deployed through a lumen within the lead 10, a catheter 30 (FIG. 6) or a similar device. The sensor 14 will be positioned and selectively covered or exposed depending upon the nature of the parameter that is sensed. For example, a mechanical pressure sensor will have some surface directly or indirectly in physical contact with the surrounding fluid medium, whereas an ultrasound sensor could be disposed entirely within the lead 10 and still provide data.

In use, the lead 10 is guided into the right atrium and the sensor 14 provides data to an external device. This data is used by the physician to manipulate and guide the lead 10 to the coronary sinus and/or confirm that the lead 10 is within the coronary sinus. Of course, the present invention could be used to navigate to any other desired anatomical location, based on appropriate sensed parameters.

In one embodiment, the sensor 14 is a temperature sensor. The temperature sensor 14 is a thermocouple, a thermistor, or any other temperature sensing device at least having sufficient ability to distinguish temperature variations within a range that is on the order of about 0.2° C., as this represents the temperature gradient about the ostium of the coronary sinus. While accurate calibration between sensed and actual temperature values is appropriate and may, in some embodiments, provide additional value, accurate sensing of temperature differentials provides sufficient basis for navigation. The temperature increase between the ostium as compared to the averaged right atrium may be used, rather than specific temperature values, in certain embodiments.

In one embodiment, the temperature sensor 14 is sufficiently sensitive and provides a sufficient signal to noise ratio to accurately detect temperature variations on the order 0.01° C. This temperature sensor 14 has a rapid response time of 50 milliseconds or better so as to provide tracking information relating to movement of the sensor 14. Finally, the temperature sensor 14 is stable so that indicated temperature variations reliably result from actual temperature differential and not from a drift in the sensor characteristics.

Figure 5A:
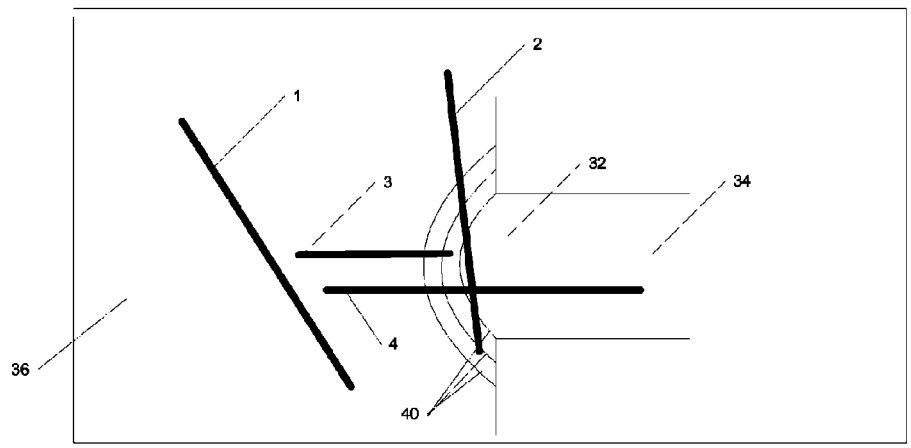
FIG. 5A illustrates sensor paths proximate the coronary sinus.

FIG. 5A is a schematic illustration of the ostium of the coronary sinus 32, with the cardiac vein 34 flowing into the right atrium 36. Various temperature bands 40 are illustrated having a common temperature, with temperature generally varying as a function of distance from the ostium 32. As the blood exits the ostium 32, it has a given average temperature. As this blood mixes with that of the right atrium, the temperature averages to the level normal within the right atrium; hence, the temperature of the blood from the coronary sinus 32 decreases as a function of distance.

Figure 5B:
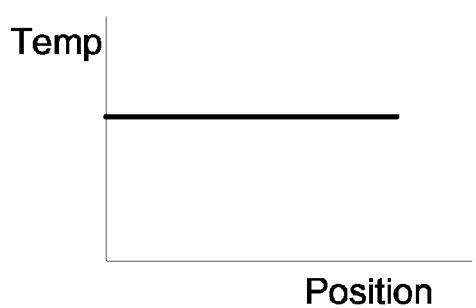
FIGS. 5B-5E are graphs relating temperature to position for the sensor paths of FIG. 5A.

Various potential paths taken by the sensor 14 when moved within the right atrium are illustrated as solid lines 1-4. Path 1 causes the sensor 14 to remain sufficiently distant from the ostium 32 so as to only detect blood temperatures in the averaged range; that is, the average temperature of blood within the right atrium. FIG. 5B is a graph of temperature versus position corresponding to path 1. As illustrated, the graph indicates a relatively constant temperature and the indication would be that the sensor 14 is not proximate to the ostium 32.

Figure 5C:
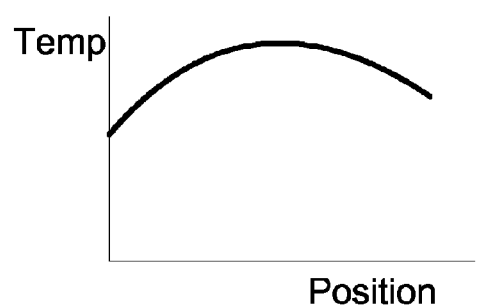
Figure 5D:
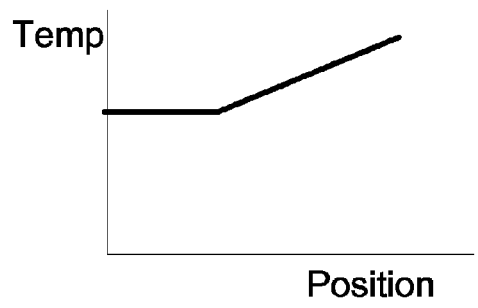
Figure 5E:
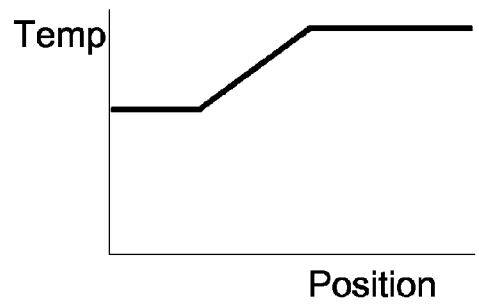

Path 2 represents movement of the sensor 14 from the right atrium past the ostium 32. The resultant temperature graph is illustrated in FIG. 5C. As shown, the temperature is initially at the averaged value, then increases until the sensor 14 is actually again moving away from the ostium 32, thus a decrease in temperature results. Path 3 represents movement of the sensor from the average temperature region directly towards the ostium 32. The temperature graph of FIG. 5D illustrates this path. The temperature is initially flat or constant and representative of the average temperature of the right atrium. As the sensor 14 approaches the ostium 32, temperature rises with a linear relationship that is proportional to distance. Path 3 is illustrated as stopping prior to reaching the ostium 32; thus, the temperature graph terminates at a higher temperature value. Path 4 is similar to path 3 but proceeds into the coronary sinus 32. This path is represented in the temperature graph of FIG. 5E. Again, the temperature remains flat or constant until the sensor 14 approaches the ostium 32. As the sensor 14 approaches the ostium of the coronary sinus 32, the temperatures rises linearly, proportional to distance. When the sensor 14 enters the ostium 32, the temperature is constant and is represented as such. Of course, this temperature value is elevated from that of the right atrium 36.

FIGS. 5A-5E represent one embodiment wherein sensor data, such as temperature data, may be used to map a portion of the right atrium 36 and/or navigate within the right atrium 36. Other physical parameters such as oxygen content, pressure, velocity, or the like may be used in a similar manner. The raw data itself may provide some useful information to the operator of the device. For example, in one embodiment the sensor 14 is used simply to confirm that the associated device, e.g., lead 10 is in fact located within the coronary sinus 32. Temperature values, or other raw data, may be used to quickly make such a conclusion. That is, the average temperature of the right atrium will be measured and hence known. The current temperature value from the sensor 14 is monitored and if elevated by a sufficient amount, e.g., about 1° C., provides a confirmation that the sensor is no longer in the right atrium. Used in conjunction with known techniques, this may establish that the sensor 14 is in the coronary sinus. Of course, other temperature differentials exist with respect to the right atrium, such as within the inferior vena cava. Therefore, the other known techniques, such as fluoroscopy establish that the sensor 14 is not in another, easily identified higher temperature area therefore establishing that the higher temperature data indicates that the sensor 14 is in the coronary sinus. In summary, the temperature values provide a confirmation that the device is within the coronary sinus.

More directional information is gathered by providing a plurality of sensors 14 that are arranged circumferentially about the lead 10, as illustrated in FIG. 2B. With such a configuration, the various sensors 14 sense in different directions. Thus, by knowing the relative positions and orientations of the various sensors 14, their varying output will provide a directional component to the gathered temperature data.

The representations provided in FIGS. 5B-5E apply to configurations having a single temperature sensor as well as multiple sensors. That is, a single sensor 14 moved along the trajectories indicated in FIG. 5A, will in fact provide the indicated results. However, with a single temperature sensor 14, it may be more difficult to determine a course of direction based upon any given data point. With multiple, directionally distinct sensors 14, each provides the above described information with the addition of a directional component. Thus, a predictive path can be plotted. For example, consider a lead 10 having multiple sensors 14 arranged in different directions, e.g., circumferentially as illustrated in FIG. 2B. If the lead 10 positioned so that is represents path 2 of FIG. 5A, then sensors 14 facing the coronary sinus 32 would sense a higher temperature than those facing the center of the right atrium.

While such raw data provides value in certain embodiments, the present invention also provides for computational analysis of this raw data to generate navigational information and/or provide for confirmation of entry. For example, by recording temperature versus position, as represented in FIGS. 5B-5E, the path and relative position of the sensor 14 can be calculated. Once the raw data is processed, the resulting navigational data may be used in a number of ways. For example, a graphical model or map is illustrated on a screen with a representation of the current sensor 14 position and the mapped anatomical features that are known, such as the coronary sinus 32. The physician then navigates based on this generated map. Alternatively, or in addition to the graphical mapping features, audible commands can be generated based on the processed data. For example, commands such as "advance," "retract," "rotate X degrees," etc. are generated by the processor. More tonal representations of the raw data may also be produced. For example, a tone is generated corresponding to the sensed temperature; as temperature increases, the frequency of the tone is increased. Thus, the physician is able to discern the relative position of the sensor 14 based on the tone or generated commands, without requiring visual confirmation of the navigational data.

Figure 7:
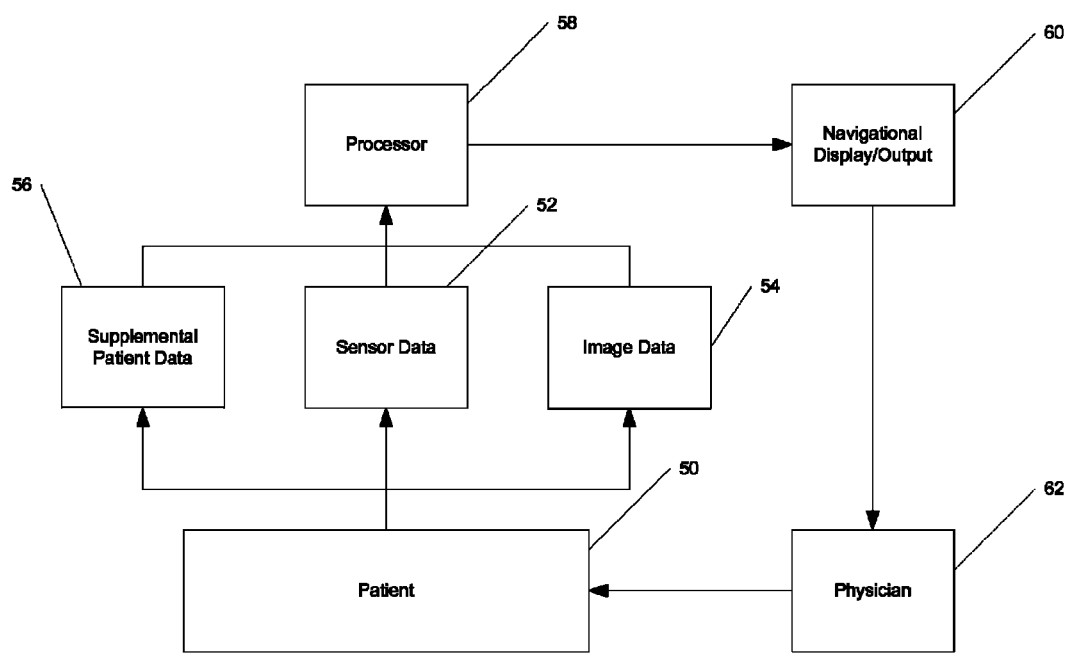
FIG. 7 is a block diagram of a system for obtaining a processing sensor data.

In one embodiment, the navigational aides are used in concert with existing medical and sensory equipment to aide the physician. FIG. 7 is a schematic illustration of such a system. The patient 50 has an appropriate device, such as lead 10, equipped with one or more sensors 14 to sense selected parameters, such as temperature. This sensor data 52 is output to a processor 58. In addition, imaging data 54 is also gathering from the patient 54. This imaging data may take any form such as MRI, fluoroscopy, CAT scans, PET scans or the like. Such imaging data may be live or current, e.g., fluoroscopy, or may have been previously captured.

The processor 58 takes the sensor data 52, and as previously discussed, generates the appropriate navigational information that is then displayed on or broadcast from a navigational display 60. The navigational display 60 is a display screen such as for example a CRT or LCD. This display 60 is viewed by the physician 62 and allows for manipulation of the lead 10 within the patient 50 in order to find, enter, and/or confirm entry into the coronary sinus.

The navigational display 60, in one embodiment, displays only information derived by the processor from the sensor data 52. In another embodiment, the derived information is correlated with image data 54 and a composite is generated. For example, current positional data from the sensor 14 and/or an identified position of the coronary sinus are superimposed or digitally combined on a given image or image feed. Thus, the normally transparent soft tissue of the coronary sinus may be represented on the image based on the processed navigational data. The particular technique used to combine the sensor data 52 and the image data 54 will vary depending upon the types of each. For example, digitally created navigational data is superimposed over an analog image source or the image data 54 is digitally captured and manipulated to form a composite with the sensor data 52.

Various other physical parameters may have an affect on the data sensed by sensor 14. For example, when sensing temperature the patient's respiration and cardiac cycle cyclically affect the temperature. Thus, supplemental patient data 56 is gathered and utilized by the processor 58 to generate the navigational information. The supplemental patient data 58 includes, for example, EEG, EKG, blood pressure, respiration rate, tidal volume, patient position/orientation, ambient temperature, patient temperature, drug/pharmacology data (type, rate, dosage, etc.), implant data (e.g., if already in place), or other parameters that would affect the sensed data 52.

The processor 58 takes the various data available to provide a useful navigational result to the physician 62. The navigational display 60 provides meaningful visual and/or audio output that assists the physician in navigating a device, such as lead 10, within the anatomy of the patient. For example, the navigation display 60 assists the physician 62 in finding and/or confirming entry into the coronary sinus. As previously explained, the sensed data 52 indicates that the device is within the coronary sinus, however such data could be the result of having the device in another anatomical feature, e.g., the inferior vena cava. The processor 58 correlates the other data to effectively rule out such options.

The present invention, in various embodiments, provides for the confirmation that the lead 10 has entered the coronary sinus. This is a valuable data point for the physician as it is often very difficult to make this determination during an implantation or other type of procedure. Expanding beyond confirmation, various embodiments provide navigation aides to assist the physician in finding the coronary sinus. As explained, temperature gradients exist about the ostium that are detectable. Other parameters such as pressure, oxygen content, etc. also serve to distinguish the ostium from the remainder of the right atrium.

The particular parameter selected determines the approximate range of usefulness for navigation purposes. For example, easily measurable temperature variations are typically detectable at a distance of about 1 cm from the ostium. Thus, to rely on temperature data alone for navigation, the sensor 14 must be relatively close to ostium to then identify and navigate to the coronary sinus. Providing more accurate sensors or providing for sensors that sense a given parameter from some distance increases the useful range.

Figure 2:
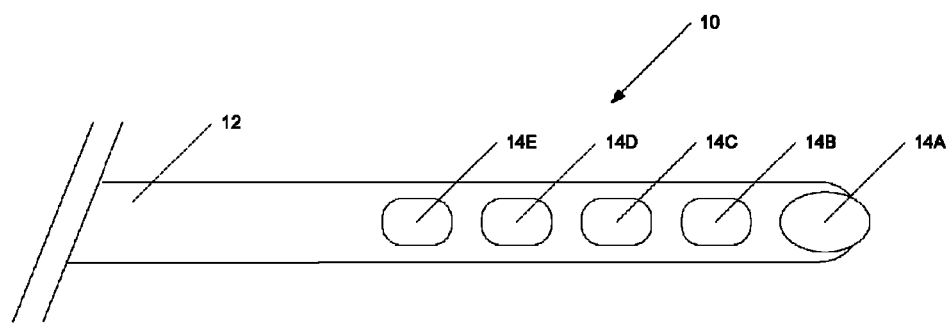
FIGS. 2A-2B are schematic illustrations of a lead having a plurality of sensors.

As previously explained, the lead 10 may be equipped with a plurality of sensors 14 (FIG. 2). Thus, as the lead 10 is manipulated to search for the coronary sinus, one or more of these sensors will likely move within the practical distance required for navigational purposes. In an alternative embodiment, sensors 14 of different types are employed. For example, flow characteristics, pressure, or chemical levels, may be monitored over a greater distance to determine a proper area and once so identified, the temperature data, is used to complete the navigation.

Figure 8:
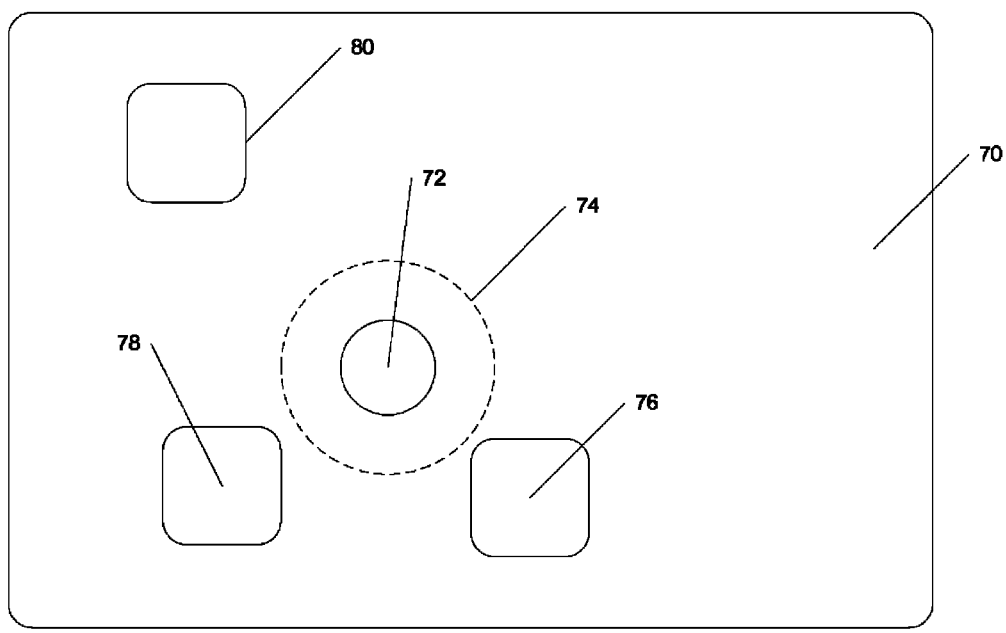
FIG. 8 is a schematic diagram illustrating anatomical positions within the right atrium.

In another embodiment, the present invention is utilized to determine an appropriate area to search, search for and identify the coronary sinus, and then navigate into the coronary sinus. FIG. 8 is a schematic, highly conceptualized two dimensional representation of a portion of the right atrium 70. The coronary sinus 72 and a target area 74 are illustrated as the desired end point and search area. The inferior vena cava 78, tricuspid valve 76, and superior vena cava 80 are also illustrated. While individual anatomy varies widely from patient to patient, certain anatomical features are generally similarly situated. For example, the coronary sinus 72 is typically disposed within an area between the inferior vena cava 78 and the tricuspid valve 76, both of which have a known proximal relationship with the super vena cava 80.

Thus, to ultimately locate the coronary sinus 72, one or more of these more easily identifiable anatomical features are first located to define the target area 74. Once the target area 74 is so identified, the physician has a general idea where the coronary sinus 72 is and uses the above described techniques to then located the coronary sinus 72.

Figure 9:
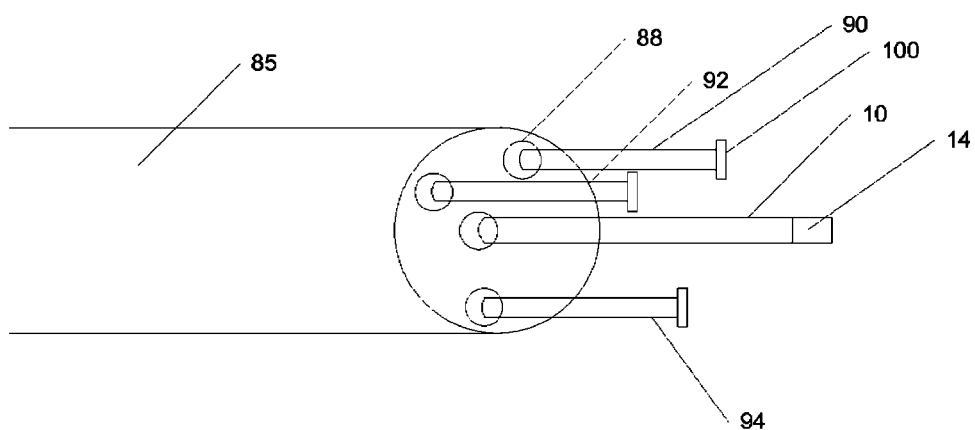
FIG. 9 is a schematic diagram of a catheter and a plurality of anchoring members.

FIG. 9 illustrates a catheter 85 that includes a plurality of lumens 88. Anchoring devices 90, 92, and 94 are each deployable through a given lumen 88. The anchoring devices 90, 92, and 94 are individually manipulated to a given anatomical feature, such as e.g., the inferior vena cava 78, tricuspid valve 76, or superior vena cava 80. Once so located, the anchoring devices 90, 92, 94 are then attached to these anatomical structures. Each anchoring device 90, 92, 94 includes an anchor member 100 that facilitates such attachment. The particular configuration of the anchor member 100 will depend upon the anatomical feature in question. The anchor member 100 could include a deployable helix, passive tines, a deployable wire loop, an actuable clamp, or other structure to temporarily secure the anchoring device in the desired area.

Figure 10:
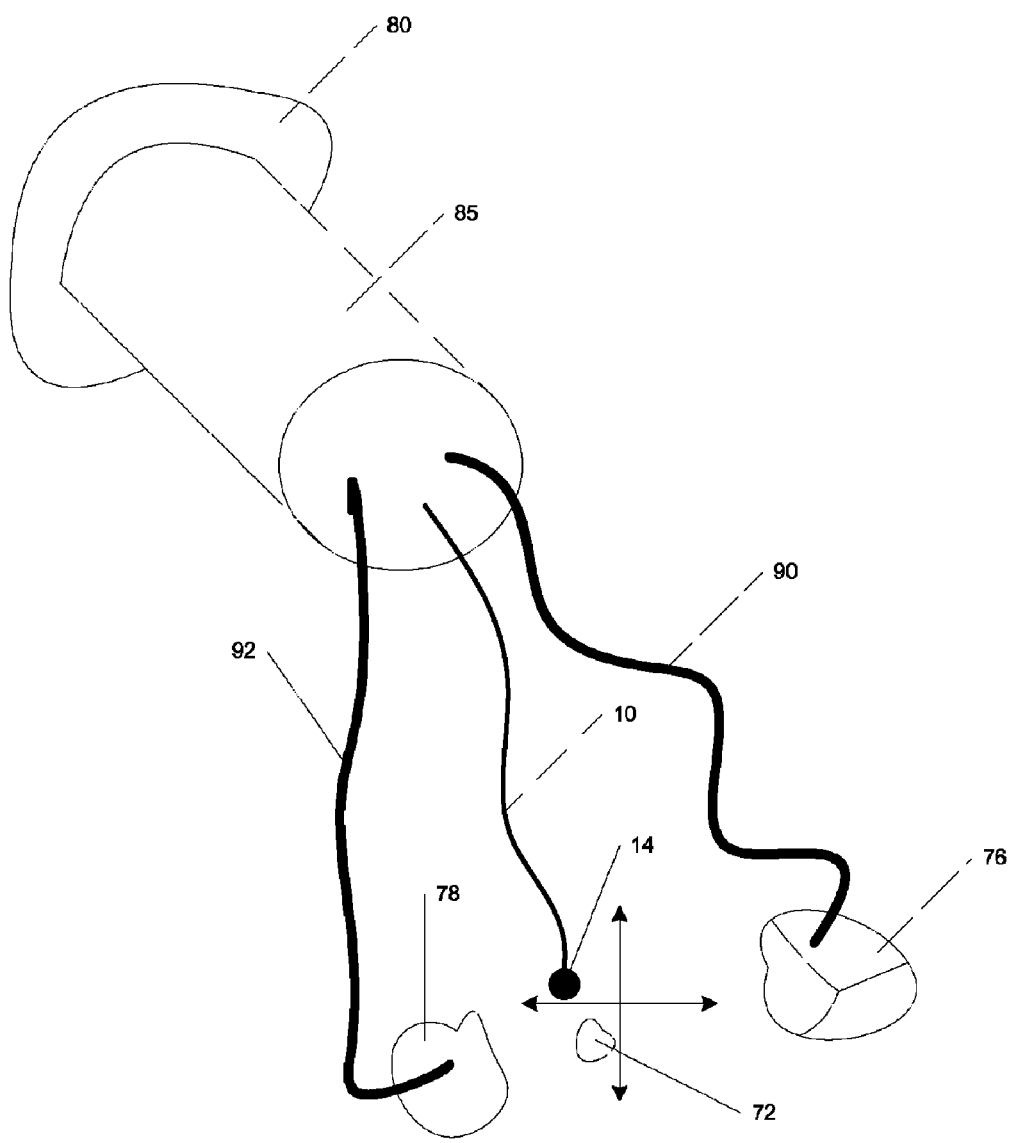
FIG. 10 is a schematic diagram of the catheter of FIG. 9 deployed within the right atrium.

Sensor 14 is deployed through the lumen 88 via an appropriate device such as lead 10, a catheter, a stylet or a similar steerable mechanism. After the anchoring members 90, 92 are secured to their respective anatomical structures, as schematically illustrated in FIG. 10, the sensor 14 is moved in the target area to locate the coronary sinus 72.

Various techniques may be employed to ultimately deliver a desired device such as a lead to the coronary sinus 72, with the various embodiments of the sensor 14. In one embodiment, the sensor(s) 14 are formed as part of the lead 10 and the lead 10 is simply deployed. Alternatively, the sensor(s) are attached to a catheter or a guidewire, which is deployed within the coronary sinus. The lead or other device is then deployed via the catheter or over the guidewire. A dedicated device having the sensor(s) 14 may be used to "map" the right atrium and identify the location of the coronary sinus. Once done, the sensor(s) 14 are removed and the lead or other device is inserted, using the known or mapped position of the coronary sinus.

Figure 11:
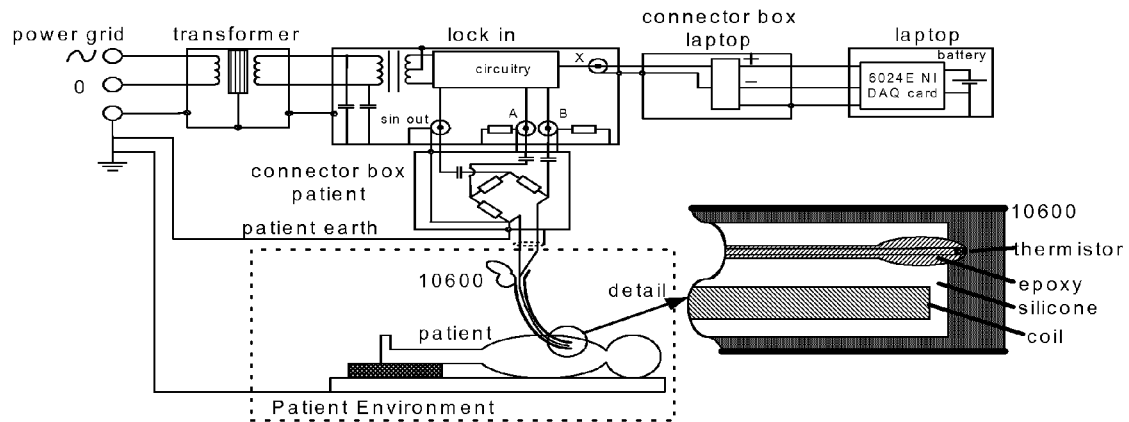
FIG. 11 is a schematic diagram illustrating one embodiment of a device having thermistor for navigating through cardiac anatomy.

FIG. 11 is a schematic diagram illustrating one embodiment of a device having thermistor for navigating through cardiac anatomy. A lead 100, or other navigable device, includes a thermistor 102 disposed near a distal end of the lead 100. The lead 100 includes sheathing 104 that may encase or, as in the illustrated embodiment, partially expose a portion of the thermistor 102 to allow for rapid response times. The thermistor 102 is electrically connected to a wheatstone bridge arrangement 106 and a lock-in amplifier 108. Such an arrangement increase the signal to noise ratio and permits improved data collection and analysis. The output from the lock-in amplifier 108 is passed to a computer 110 for processing and subsequent display.

In this embodiment, the lock-in amplifier 108 measures a relatively small signal despite significant noise by taking advantage of an AC character of the signal. The illustrated embodiment measures the resistance changes of the thermistor 102 that forms portion of the wheatstone bridge 106, with the lock-in amplifier 108 providing an AC signal. The lock-in amplifier 102 provides a reference signal at the same frequency of the sensed signal with a constant phase difference via a phase locked loop. Demodulating the signal creates a DC signal that is proportional to the original AC signal. By passing this signal through a low pass filter, only a DC signal remains that is proportional to the sensed signal. The noise is determined by the bandwidth of the low pass filter. Such an arrangement provides fast response times and accurately measures temperature differential in the necessary range.

As described above, a temperature sensor 14 or other type of sensor is utilized to navigate to or confirm the location of a given anatomical feature, such as the coronary sinus. The sensor 14 may be disposed on a device that is utilized and then removed from the patient. Alternatively, the sensor 14 is incorporated on, e.g., a lead that is ultimately implanted and thus remains in the patient for an extended period of time. As such, the temperature sensor 14 could then provide temperature data, as desired, over the lifetime of the implantation. Finally, a temperature sensor may be implanted at a desired location without providing the navigational information previously discussed.

During use, and particularly when chronically implanted, the sensor 14 will be exposed to a hostile biological environment. As such, it may be desirable to hermetically seal the sensor 14. In certain embodiments, this presents little issue. For example, an ultrasound sensor may be completely enclosed and hermetically sealed without adversely affecting performance. Temperature sensors, on the other hand, may be affected by the housing that they are contained within. As explained, because temperature data often varies based upon cyclic physiological phenomenon (e.g., different stages of a cardiac cycle) having a short time duration, a rapid response time is desired in certain embodiments. In addition, an appropriate degree of accuracy should be maintained; however, whether this accuracy is in relative terms and/or based on a relationship to calibrated values will depend upon the end use of the data. Thus, it may be difficult to hermetically seal a temperature sensor while providing sufficiently rapid response times, accurate sensing, and inhibit drift or other errors imposed by the thermal mass of the housing or enclosure.

Figure 12:
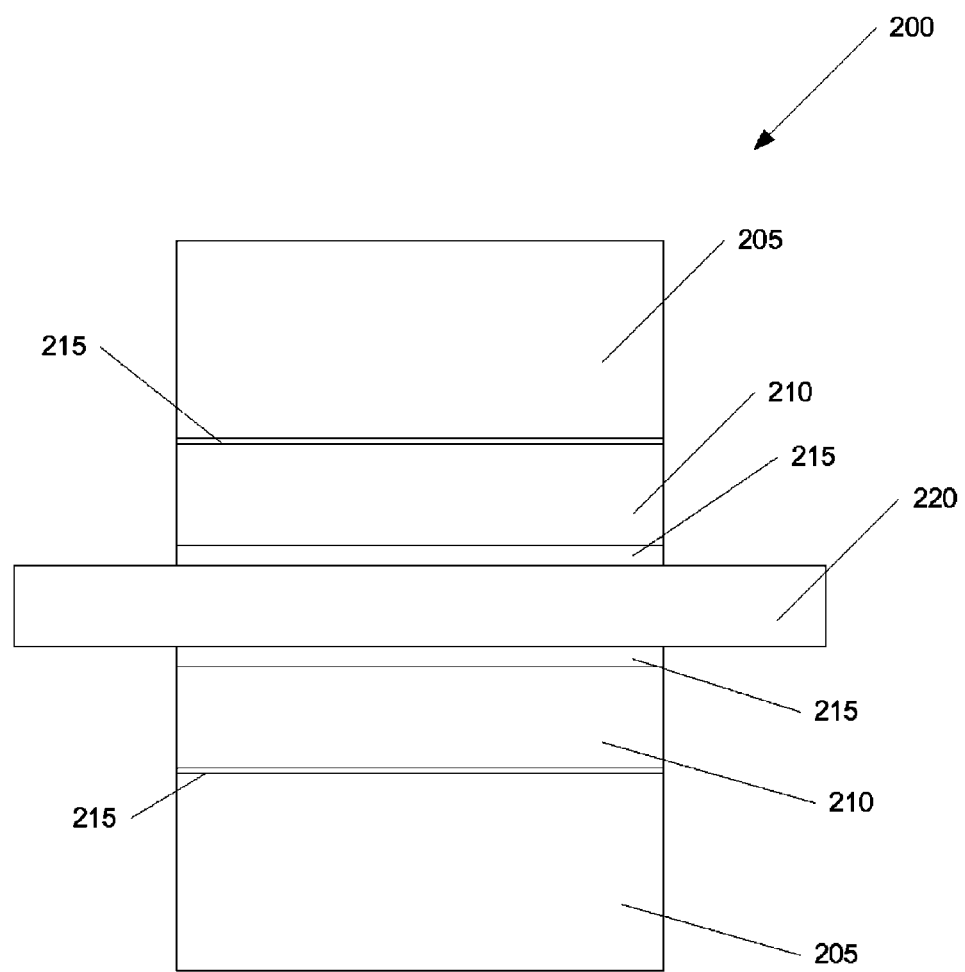
FIG. 12 is a schematic illustration of a feedthrough assembly for hermetically encasing a sensor.

The present invention provides for a feedthrough 200, as illustrated in FIG. 12, that hermetically seals a temperature sensor, provides appropriate response times, and/or insulates the sensor from the thermal effects of the surrounding housing or enclosure. The basic structure includes a housing 205, which forms the main portion of the device incorporating the feedthrough 200. For example, feedthroughs are often provided on the housing or can of an implantable pulse generator or defibrillator to provide isolated electrical connections. In such an application, the housing 205 would be an appropriate metal such as titanium. If the feedthrough 200 is incorporated into a lead or similar structure, then the housing material would correspond to that structure.

Typically, the feedthrough 200 includes a two piece sleeve 215 made from a material that can be hermetically bonded to the housing 205. For example, sleeve 215 may be made from gold or other suitable metals that can be welded to the housing 205. If non-metals are utilized, the appropriate bonding agents and/or techniques are utilized. Disposed between an inner and outer portion of the sleeve 215 is an insulator material 210. As feedthroughs 200 are commonly used to provide electrical connections, the insulator 210 is selected to act as a dielectric material in such contexts. In the present embodiment, insulator 210 is selected to provide thermal insulation in addition to or in lieu of electrical insulation. That is, the present invention may be utilized with existing feedthrough assemblies so that the materials will be selected for multiple purposes. Alternatively, the feedthrough assembly could be fabricated specifically for the purpose of encasing a sensor; thus, the material selections would be made accordingly for that purpose. Insulator 210 may be sapphire, glass, ceramic, or other materials having the desired thermal characteristics.

A pin 220, generally formed from metal, is disposed within the inner portion of sleeve 215. The pin 220 is welded to the sleeve 215, held in place via a friction fit, or otherwise secured. The pin 220 provides electrical contact while remaining electrically isolated from the housing because of the insulator 210. Here, the insulator serves to thermally isolate the pin 220 from the housing 205, while maintaining a hermetic seal.

An appropriate temperature sensor 230 is disposed within the pin 220, as illustrated in the various embodiments of FIGS. 13A-13E. The temperature sensor 230 is a thermistor or other appropriate temperature sensing element having the appropriate electrical contacts or wires 235 extending out from the pin 220. The pin 220 has a hollow interior to receive the sensor 230 or the temperature sensor 230 is formed as an integral component of the pint 220 during manufacture.

Figure 13A:
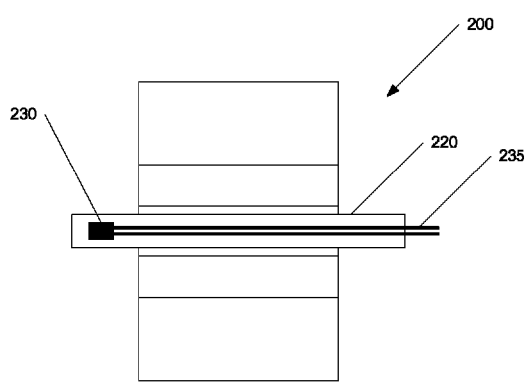
FIGS. 13A-13E are partially sectional, side elevational views of a temperature sensor within a pin of a feedthrough assembly.

As illustrated in FIG. 13A, the pin 220 extends some distance beyond the housing 205. The pin 220 is thermally insulated from the housing 205 via the insulator 210. Thus, the medium surrounding the extended portion of the pin 220 will affect the temperature. As indicated, the pin 220 may be made from metal, composites, ceramics or other suitable materials. The particular material choice will determine the temperature response time but because of the thermal insulation and the small size of the pin (relative to the sensor 230) the response time will be relatively rapid. As such, the sensor 230 will likewise have a rapid response time while responding within the pin 220. In other words, the pin 220 serves to hermetically isolate the sensor 230 while adding little thermal mass to act as a barrier between the sensor 230 and the medium being sensed. In some embodiments, the pin 220 is in contact with the sensor 230 and thus, acts as a thermal conductor.

Figure 13B:
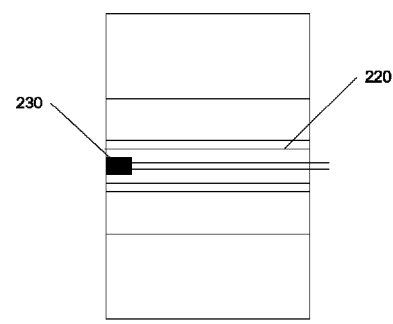

FIG. 13B illustrates an embodiment wherein the pin 220 is flush with the housing 205. The contact with the sensed medium is thus limited to surface area of the exposed end of the pin 220. This embodiment may be useful where protrusion from the housing is undesirable. For example, lateral extension from a lead or similar structure may hinder movement during implantation. In other embodiments, the pin 220 is remotely deployable from the position illustrated in FIG. 13B to that of FIG. 13A.

Figure 13C:
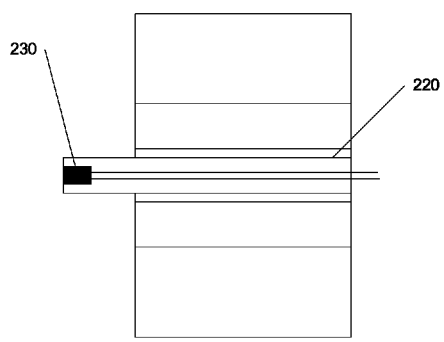

The embodiment of FIG. 13C is similar to that of FIG. 13A except for the position of the sensor 230 relative to the exposed surface of the pin 220. As illustrated, the sensor 230 may abut the end or may be retracted some distance from the end of the pin 220. Direct contact between the sensor 230 and the pin 220 will allow the sensor 230 to respond more rapidly to temperature fluctuations within the surrounding medium. Though not illustrated, the same variation is permissible with respect to circumferential engagement of the sensor 230 to the interior lateral sidewalls of the pin 220. That is, the sides of the sensor 230 may abut the interior sidewalls of the pin 220 at selected points or along the entire perimeter. As illustrated, both the pin 220 and the sensor 230 are cylindrical. Other shapes may be selected that may or may not be complementary and would affect the amount of contact permissible between the two components.

Figure 13D:
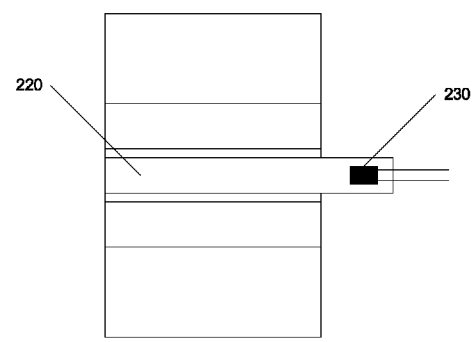

FIG. 13D illustrates an embodiment wherein the sensor 230 is distant from the sensed medium. The pin 220 effectively acts as an extension of the sensor 230 and conducts heat to and away from the sensor 230. The pin 220 is illustrated as being flush with the portion of the housing exposed to the medium but could just as well extend outward. In some cases, existing feedthroughs 200 could be retrofit to include the sensor 230 bored a minimal distance into the pin 220 or simply attached to an end of the pin 220. This embodiment would also be useful when the pin material is not conducive to incorporating a hollowed interior. Distance from the medium to the sensor 230 is increased with respect to the other embodiments; however, the actual scale employed in practice is small. Thus, with the proper material choices for the pin 220 (e.g., good thermal conductor) and an effective insulator 210, the sensor 230 is capable of detecting the temperature of the sensed medium with an acceptable degree of accuracy within a sufficiently rapid response time.

Figure 13E:
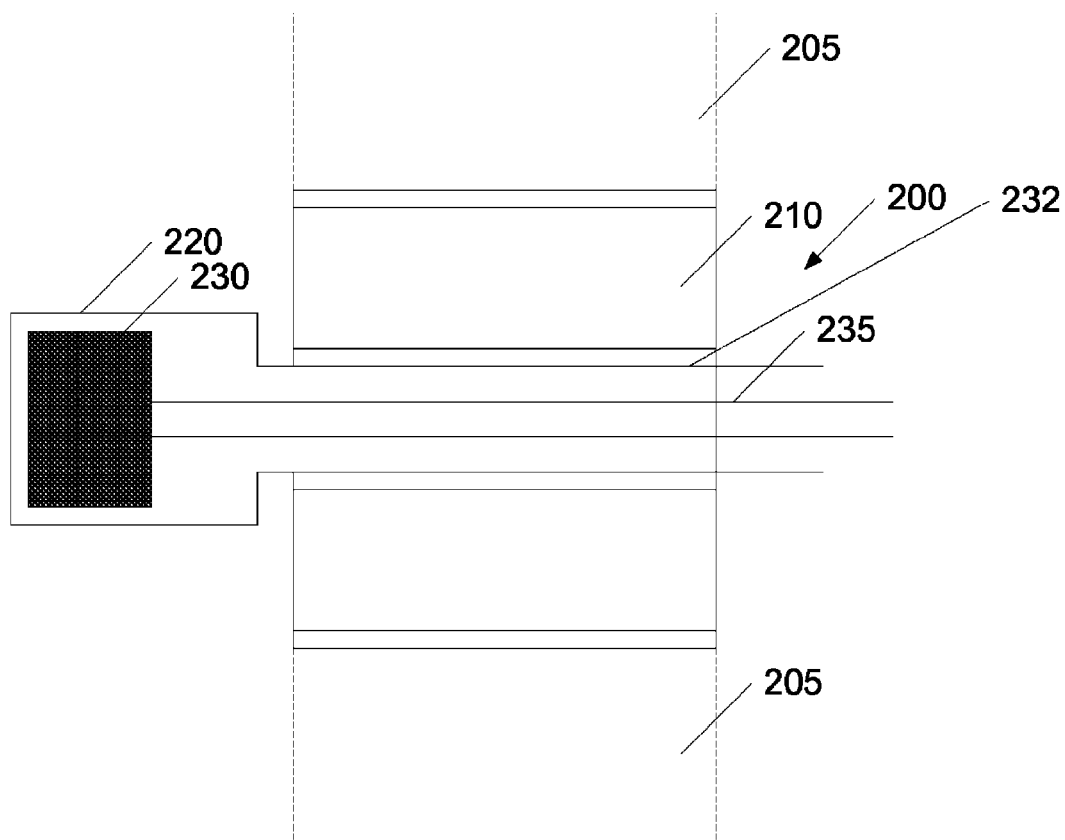

FIG. 13E illustrates an embodiment wherein the sensor 230 contained within the pin 220 has a larger diameter than the throughbore 232 within the insulator 210 that receives the pin 220. Thus, the pin 220 does not have to have a uniform diameter; rather, different sizes, shapes and configurations may be achieved while retaining thermal isolation from the housing 205 via the insulator 210. In this manner, sensors 230 of various sizes may be utilized with feedthrough assemblies 200 employing otherwise standard dimensions.

Figure 14A:
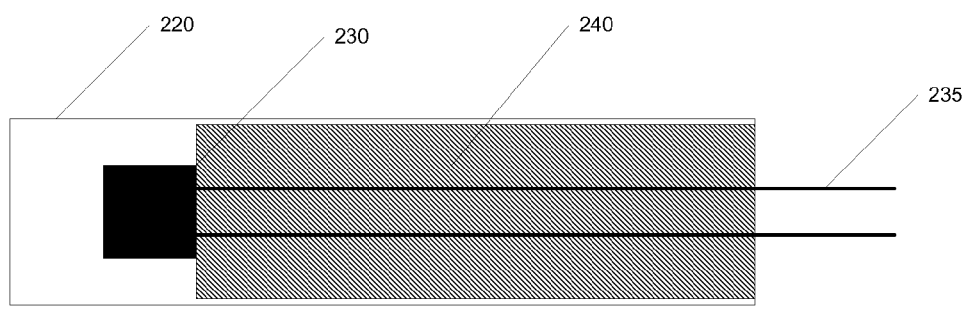
FIGS. 14A-14B illustrate a feedthrough pin having a sensor and including thermal insulative material.
Figure 14B:
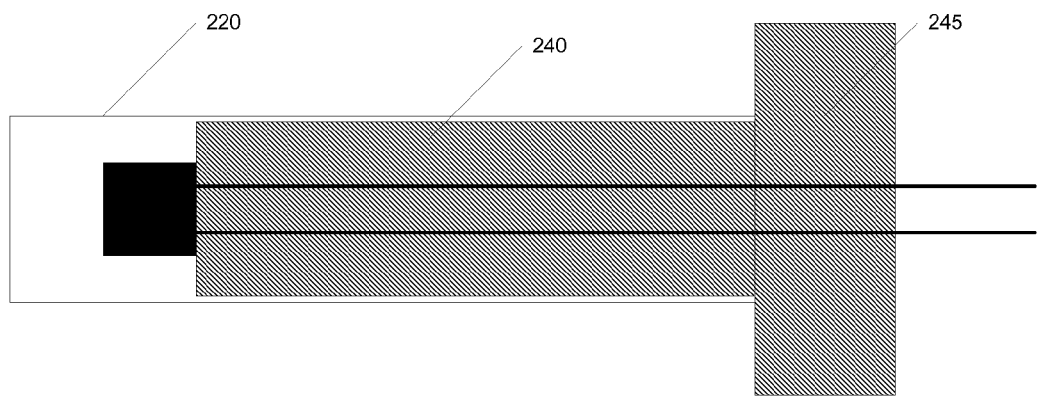

FIGS. 14A and 14B illustrate the addition of a thermal insulating material 240 within the interior portion of the pin 220. The thermal insulating material 240 will inhibit heat transfer with the interior of the housing 205. That is, even though the insulator 210 thermally isolates the contact areas of the relevant components, at least a portion of the pin 220 is exposed to the interior of the housing assembly 205. In some embodiments, a substantial portion of the pin 22 is actually exposed to the interior of the housing 205. Depending upon what the housing 205 is, that exposure may or may not facilitate heat transfer. For example, when the housing 205 is an implantable device the interior is typically filled with inert gases such as argon or nitrogen. The thermal insulating material 240 will greatly reduce or eliminate heat transfer that might otherwise occur from the interior of the housing 205 to the sensor 230 via the pin 220. In FIG. 14B additional insulating material 245 abuts the interior end portion of the pin 220 providing yet another thermal barrier.

A chronically implanted temperature sensor 230 provides for a number of applications. The sensor 230 is implanted anywhere within the anatomy where temperature data is desired. For example, temperature fluctuations within portions of the cardiac anatomy are representative of the cardiac cycle. Typically, the cardiac cycle is monitored via electrical signals obtained from implanted leads or external sensors (e.g., EKG). Thus, temperature sensing provides an alternative choice to obtain the same data. In addition, the temperature data may be used in conjunction with the electrical data as a means of confirmation. Finally, the temperature data may be used when the electrical data is unavailable. For example, pacing pulses often inhibit sensing on the same or nearby electrodes for a period of time; thus, it is sometimes difficult to sense subsequent electrical events or to determine if capture occurred. As the temperature data would be unaffected by the electrical stimulation, this data can be used to monitor the cardiac cycle during refractory periods for the leads or at any time electrical data is unavailable.

While sensor 230 has been illustrated as a temperature sensor, other types of sensors may be incorporated into the pin 220 of the feedthrough 200. FIG. 15 illustrates an embodiment wherein the pin 220 acts as a pressure transducer. In this embodiment, the pin 220 has a hollow interior filled with an appropriate fluid medium 260 in a compressed state. The distal end of the pin 220 is a flexible membrane 270 that is in contact with the sensed medium, e.g., blood within a given cardiac chamber or within a portion of the venous anatomy. In summary, the pressure variations of the external medium displace the membrane 270, which translates through the interior fluid medium 260. The interior fluid medium 260 causes a proportional displacement of an interior sensing membrane 275. This proportional movement, displacement, or resultant force is sensed by an appropriate optical, mechanical, or electromechanical sensor 285. This sensed data is correlated to a pressure of the surrounding exterior medium, e.g. blood.

Furthermore, by increasing the surface area of the interior membrane 275 relative to the surface area of the exterior membrane 270, mechanical amplification is achieved. That is, the interior fluid medium 260, as indicated, is in a compressed state. Thus, displacement of the exterior membrane 270 will result in a uniform pressure differential that is applied with the same force across the larger surface area of the interior membrane 275. Thus, smaller pressure differentials in the medium are more easily sensed and measured.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

The invention claimed is:

1. An implantable medical device comprising:
   a feedthrough assembly coupled to an opening of a housing of the implantable medical device and partially extending from an interior of the housing to an exterior of the housing; and
   a plurality of sensors circumferentially disposed within the feedthrough assembly within the portion of the feedthrough assembly partially extending to the exterior of the housing, wherein the plurality of sensors are configured to generate a directional signal as a function of an orientation and relative position of each of the plurality of sensors.

2. The device of claim 1, wherein the implantable medical device comprises at least one of a pacemaker, a cardioverter, or a defibrillator, and the housing contains a pulse generator configured to produce electrical stimulation via one or more electrodes.

3. The device of claim 1, wherein the implantable medical device comprises a lead that comprises the housing.

4. The device of claim 1, wherein the feedthrough assembly further includes a pin having a hollow interior and the plurality of sensors is disposed within the hollow interior.

5. The device of claim 4, wherein the plurality of sensors is disposed in the hollow interior of the pin.

6. The device of claim 4, further comprising a thermal barrier disposed within the hollow interior and isolating the plurality of sensors from an interior of the housing.

7. The device of claim 6, wherein the thermal barrier extends beyond the hollow interior of the pin and into the interior of the housing.

8. The device of claim 4, further comprising a sleeve outer portion hermetically bonded to the housing and disposed between the pin and the housing.

9. The device of claim 8, further comprising a thermal insulator disposed within the sleeve outer portion.

10. The device of claim 9, further comprising a sleeve inner portion disposed between the pin and the thermal insulator.

11. An implantable medical device, comprising:
    a feedthrough assembly coupled to a housing of the implantable medical device and partially extending from an interior of the housing to an exterior of the housing;

a plurality of sensors extending through an opening in the housing into a portion of the feedthrough assembly extending outside of the housing, wherein the plurality of sensors are circumferentially disposed within the feedthrough assembly and are configured to generate a directional signal as a function of an orientation and relative position of each of the plurality of sensors; and means for hermetically sealing the feedthrough assembly to the housing.

12. The device of claim 11, further comprising a pin disposed within the feedthrough assembly that includes a hollow interior and the plurality of sensors is disposed within the hollow interior.

13. The device of claim 12, wherein the plurality of sensors is in contact with an interior surface of the pin.

14. The device of claim 12, further comprising a thermal barrier disposed within the hollow interior and isolating the plurality of sensors from an interior of the housing.

15. The device of claim 14, wherein the thermal barrier extends beyond the hollow interior of the pin and into the interior of the housing.

16. The device of claim 12, wherein the means for hermetically sealing the feedthrough assembly to the housing comprises a sleeve outer portion hermetically bonded to the housing and disposed between the pin and the housing.

17. The device of claim 16, further comprising a thermal insulator disposed within the sleeve outer portion.

18. The device of claim 17, further comprising a sleeve inner portion disposed between the pin and the thermal insulator.

19. An implantable medical device comprising:
a feedthrough assembly coupled to an opening of a housing of the implantable medical device and partially extending from an interior of the housing to an exterior of the housing;
a plurality of sensors circumferentially disposed within the feedthrough assembly such that at least a portion of the plurality of sensors extends outside of the housing, wherein the plurality of sensors are configured to generate a directional signal as a function of an orientation and relative position of each of the plurality of sensors; and
means for hermetically sealing the feedthrough assembly to the housing.

20. An implantable medical system comprising:
an implantable medical device, having:
a feedthrough assembly coupled to an opening of a housing of the implantable medical device and partially extending from an interior of the housing to an exterior of the housing,
a plurality of sensors circumferentially disposed within the feedthrough assembly within the portion of the feedthrough assembly partially extending to the exterior of the housing, wherein the plurality of sensors are configured to generate a directional signal as a function of an orientation and relative position of each of the plurality of sensors; and
a processor configured to analyze the signals generated by the plurality of sensors and to correlate a result of the analysis with mapped anatomical features to generate navigational data.

21. The implantable medical system of claim 20, further comprising a graphical display for mapping the navigational data.

* * * * *